United States Patent [19]
Palazzini et al.

[11] Patent Number: 6,080,732
[45] Date of Patent: Jun. 27, 2000

[54] USE OF SULODEXIDE AND OF THE MEDICINES CONTAINING IT IN THE TREATMENT OF THE DIABETIC RETINOPATHY

[75] Inventors: Ernesto Palazzini; Flavia Rubbi, both of Bologna, Italy

[73] Assignee: Alfa Wassermann S.p.A., Pescara, Italy

[21] Appl. No.: 09/266,385

[22] Filed: Mar. 11, 1999

[30] Foreign Application Priority Data

Apr. 15, 1998 [IT] Italy .................. B098A0239

[51] Int. Cl.⁷ .................. A61K 31/725; A61K 31/70
[52] U.S. Cl. .................. 514/56; 514/52
[58] Field of Search .................. 514/56, 52

[56] References Cited

U.S. PATENT DOCUMENTS 5,496,807 3/1996 Marchi et al. .................. 514/52

*Primary Examiner*—Theodore J. Criares
*Assistant Examiner*—Jennifer Kim
*Attorney, Agent, or Firm*—Bucknam and Archer

[57] ABSTRACT

The use of sulodexide, a glycosaminoglycan of natural origin extracted from mammalian intestinal mucosa, and of medicines containing it in the treatment of patients suffering from retinopathy of diabetic origin is the object of the present invention.

The effectiveness of sulodexide has been proved by the significant lowering of the plasmatic exudation and of the hard exudates, by the improvement of the retinic lesions and by the restoration of the functional integrity of the membrane of the microcapillaries with subsequent decrease of the capillary permeability in diabetic patients treated with pharmaceutical compositions containing therapeutically effective amounts of drug.

4 Claims, No Drawings

USE OF SULODEXIDE AND OF THE MEDICINES CONTAINING IT IN THE TREATMENT OF THE DIABETIC RETINOPATHY

BACKGROUND OF THE INVENTION

The diabetic retinopathy is the main cause of blindness in the occidental world even if most diabetics do not become blind.

The first signs of the retinic change consist in the increase of the capillary permeability shown by the loss of the colouring matter within the vitreous humour after a fluorescein injection. Subsequently the occlusion of the retinic capillaries occurs with consequent formation of aneurysms sack- and spindle-shaped; moreover arteriovenous deviations can also occur.

The vascular lesions are accompanied by the proliferation of sprouts of endothelium cells and by the loss of the pericytes that surround and support the blood vessels.

Punctiform haemorrhages occur in the inner retinic areas, while the bleeding at the level of the more superficial layer of the nervous fibres causes lesions in the shape of flame, stain or line, while the pre-retinic haemorrhages show a typical look in the shape of a boot.

The diabetic retinopathy causes also two kinds of exudates: cottony exudates and hard exudates.

The first ones are individuated by the angiography as microinfarcts, i.e. as areas not sprinkled surrounded by a ring of broken capillaries. A sudden increase of the number of the cottony exudates represents a signal of unfavourable prognosis and can be the warning of a quick progression of the retinopathy.

The hard exudates are more common than the cottony exudates and indicate the leakage of serum proteins and of lipids from the damaged capillaries.

The vitreous haemorrhage and the detachment of the retina are the most severe complications of the diabetic retinopathy: a sudden loss of the visus in an eye is almost always caused by one of these lesions.

The frequency of the diabetic retinopathy depends on the duration of the diabetic disease; about 85% of the diabetic people suffers from retinopathy even if ophthalmologically distinguishable lesions do not sometimes appear also after 30 years of diabetes.

One of the mechanisms discovered by Hansen C. et al. on Horm. Metab. Res., 27, (12), 555–8, (1995) as a cause of the development of the diabetic microangiopathy lies in the lowering of the amount of glycosaminoglycans, heparan sulfates and dermatan sulfates, within the basal membrane of the capillary endothelium with consequent increase of the vasal permeability.

This mechanism has been described also in the retinic microvessels, mainly in the arterioles, and is considered one of the first steps in the development of the retinopathy. Tamsma J. T. et al. on Diabetologia, 37 (3), 313–20, (1994) showed how the decrease of the glycosaminoglycans, mainly of the heparan sulfate, is responsible for the change of the anionic charge in the glomerular basal membrane with consequent proteinuria and Cruickshanks K. J. et al. on Ophthalmology, 100, 862–7, (1993) have shown the relation between microalbuminuria and diabetic retinopathy that explains both the breakage of the haemato-retinic barrier and the plasmatic exudation in the retina.

U.S. Pat. No. 5,496,807 showed how the administration of sulodexide, a glycosaminoglycan made by a heparin like fraction and by dermatan sulfate, has significantly reduced the excretion of albumin in diabetic patients not dependent from insulin.

The effect of the administration of the sulodexide to patients suffering from diabetic retinopathy has now been investigated on the ground of the described observations.

DESCRIPTION OF THE INVENTION

The therapeutic use of the sulodexide, glycosaminoglycan of natural origin extracted from mammalian intestinal mucosa having a sulfation degree and an anticoagulant activity lower than those of the heparin, and of the medicinal specialities containing it, in the treatment of patients suffering from diabetic retinopathy is the object of the present invention.

The present invention represents an overcoming of the teachings of the prior art because a real therapeutical effectiveness in man of a drug widely used for a long period of time in pathologies completely different from the diabetic retinopathy is proven.

The diabetic retinopathy is a clinically well defined pathology, characterized by lesions to the retina coupled with haemorrhages, exudated, scars, proliferation of blood vessels that can bring till the haemorrhage of the vitreous body and the detachment of the retina.

It has now been found that the administration of pharmaceutical compositions containing therapeutically effective amounts of sulodexide to diabetic patients suffering from retinopathy has brought to a remarkable improvement of the retinic lesions clearly ascertainable just after 8 weeks of treatment with decrease of the vascular exudates and of the hard exudates.

A significant decrease of vascular exudates in 18 out of 20 eyes of 10 patients submitted to the treatment with sulodexide has been verified at the end of the treatment lasted 4 months. The hard exudates have decreased in 8 out of 20 eyes, the retinic lesions have improved in most patients and, anyway, during the treatment a progress of the retinic lesions has been observed in no case. The effectiveness of the treatment has been checked by means of retinography, fluoroangiography and control of the glycosylated haemoglobin.

The results obtained show the effectiveness of the use of therapeutically effective amounts of sulodexide in the treatment of patients suffering from diabetic retinopathy for the restoration of the functional integrity of the basal membrane of the retinic capillaries endangered from the increase of the capillary permeability caused by the loss of glycosaminoglycans caused by the diabetic pathology, while the metabolic control has always been good along the whole period of observation.

The sulodexide can be administered under many kinds of pharmaceutical compositions administrable both for oral route and for subcutaneous, intramuscular and intravenous routes during the treatment of the diabetic retinopathy.

The pharmaceutical compositions administrable by oral route preferred in carrying out the present invention are capsules, made by soft or hard gelatine, gastroresistant capsules, tablets, controlled release tablets, gastroresistant tablets, granulates and syrups.

The dosage, depending on the body weight and the seriousness of the illness, is comprised between 500 L.S.U. (lipasaemic units) and 2000 L.S.U. a day.

The test to which 10 diabetic patients both males and females suffering from diabetic retinopathy have been submitted has been carried out by administering for 4 months to the patients 1000 L.S.U. of sulodexide a day in the form of 2 capsules of VESSEL DUE F® containing 250 L.S.U. twice a day.

The description of the test is given to further illustrate the invention and has not to be taken as a limitation of the invention itself.

EXAMPLE 1

Ten adult diabetic patients, 6 men and 4 women, aged between 35 and 65 years, suffering from diabetes mellitus, 3 out of them insulin-dependent (IDDM) and 7 not insulin-dependent (NIDDM), suffering from diabetic retinopathy have been treated twice a day with 2 capsules of VESSEL DUE F®, totalling a daily dose equal to 1000 L.S.U. for a continuative period of 4 months.

Patients submitted to previous treatment of the retinopathy with laser have been excluded from the test.

The patients have been submitted to fluoroangiographic examination and to retinography immediately before the therapy (time T Ø), after 2 months of treatment (time T 1) and after 4 months of treatment, i.e. at the end of the treatment period (time T 2). Moreover a dosage of the glycosylated haemoglobin has been carried out at every check. The fluoroangiography and the retinography have been carried out according to standard methods and the photograms have been graduated by giving a score to the plasmatic exudation (Pe) and to the hard exudates (He) on the basis of the ETDRS Classification by observers unaware of the aim of the study, as reported from ETDRS Report Number 10 on Ophthalmology, 98, 786–806, (1991) and from ETDRS Report Number 11 on Ophthalmology, 98, 807–822, (1991).

All patients have well borne without adverse reactions the 4 months period of treatment with VESSEL DUE F® completing the test.

The determination of the glycosylated haemoglobin has shown how the metabolism has been constantly kept good along the whole treatment period.

The fluoroangiographic examination showed after 2 months of treatment (T 1) a remarkable improvement of the retinic lesions with decrease of the plasmatic exudation in 15 eyes out of 20 and of the hard exudates in 4 eyes out of 20.

At the end of the treatment the improvement came out to be even more evident with a decrease of the plasmatic exudation in 18 eyes out of 20 and of the hard exudates in 8 eyes out of 20.

The classifications used to evaluate the hard exudates and the leakage according to the schemes suggested by the ETDRS are reported in the below reported TABLE 1.

In particular the scores have the following meaning for the hard exudates:

0=imperceptible
1=hardly perceptible or dubious
2=moderate
3=numerous

The scores have the following meaning for the leakage:

0=imperceptible
1=hardly perceptible or dubious
2=definite
3=with cystoid spaces

TABLE 1

| | | | Right Eye | | | | | | Left Eye | | | | | |
|---|---|---|---|---|---|---|---|---|---|---|---|---|---|---|
| | | | Pe | | | He | | | Pe | | | He | | |
| Age | Sex | Kind of diabetes | T0 | T1 | T2 | T0 | T1 | T2 | T0 | T1 | T2 | T0 | T1 | T2 |
| 35 | m | IDDM | 3 | 2 | 1 | 2 | 1 | 1 | 2 | 2 | 1 | 2 | 2 | 1 |
| 42 | f | IDDM | 3 | 2 | 2 | 2 | 2 | 1 | 3 | 2 | 2 | 3 | 3 | 2 |
| 48 | f | IDDM | 2 | 1 | 0 | 1 | 1 | 1 | 2 | 1 | 1 | 2 | 1 | 1 |
| 60 | m | NIDDM | 1 | 1 | 1 | 0 | 0 | 0 | 2 | 1 | 1 | 0 | 0 | 0 |
| 52 | m | NIDDM | 2 | 0 | 0 | 1 | 1 | 1 | 2 | 1 | 1 | 1 | 1 | 1 |
| 61 | m | NIDDM | 3 | 2 | 2 | 2 | 2 | 1 | 3 | 2 | 1 | 3 | 2 | 2 |
| 65 | m | NIDDM | 2 | 1 | 0 | i | 1 | 1 | 2 | 2 | 1 | 0 | 0 | 0 |
| 57 | m | NIDDM | 3 | 2 | 1 | 3 | 2 | 2 | 3 | 2 | 2 | 2 | 2 | 2 |
| 57 | f | NIDDM | i | 1 | 1 | 1 | 1 | 1 | 2 | 1 | 1 | 1 | 1 | 1 |
| 59 | f | NIDDM | 3 | 2 | 1 | 1 | 1 | 1 | 1 | 1 | 0 | 0 | 0 | 0 |
| Average | | | | | | | | | | | | | | | |
| 53.6 | | | 2.3 | 1.4 | 0.9 | 1.4 | 1.2 | 1 | 2.2 | 1.5 | 1.1 | 1.4 | 1.2 | 1 |
| AES | | | | | | | | | | | | | | | |
| 2.97 | | | 0.26 | 0.22 | 0.23 | 0.27 | 0.2 | 0.15 | 0.2 | 1.17 | 0.18 | 0.37 | 0.33 | 0.26 |
| P (vs. T0)* | | | | 0.007 | 0.008 | | NS | 0.046 | | 0.008 | 0.002 | | NS | 0.046 |
| P (vs. T1)* | | | | | 0.25 | | | NS | | | 0.046 | | | NS |
| P** | | | | | 0.0006 | | | 0.05 | | | 0.003 | | | 0.05 |

\* = Wilcoxon Signed-Ranks test
\*\* = Friedman Anova
Pe = Plasmatic exudation
He = Hard exudates
NS = Not significative

What is claimed is:

1. A method of treatment of diabetic retinopathy which consists of administering to a patient suffering from diabetic retinopathy a therapeutically effective amount of sulodexide.

2. The method according to claim 1 wherein the amount of sulodexide is comprised between 500 L.S.U. and 2000 L.S.U.

3. The method according to claim 1 wherein sulodexide is administered by oral route.

4. The method according to claim 1 wherein sulodexide is administered by subcutaneous, intramuscular or intravenous route.

\* \* \* \* \*